United States Patent [19]

Jozic

[11] 4,372,955

[45] Feb. 8, 1983

[54] ANTI-ARRYTHMIC SULPHONAMIDE COMPOSITIONS

[75] Inventor: Ljerka Jozic, Hanover, Fed. Rep. of Germany

[73] Assignee: Johann A. Wuelfing, Fed. Rep. of Germany

[21] Appl. No.: 357,468

[22] Filed: Mar. 12, 1982

Related U.S. Application Data

[62] Division of Ser. No. 148,139, May 9, 1980, abandoned.

[30] Foreign Application Priority Data

May 16, 1979 [GB] United Kingdom ............... 7917035

[51] Int. Cl.$^3$ ................ A61K 31/495; A61K 31/445; A61K 31/40
[52] U.S. Cl. ................................... 424/250; 424/267; 424/274; 544/398; 546/205; 546/206; 548/569
[58] Field of Search ................... 424/267, 250, 274

[56] References Cited

U.S. PATENT DOCUMENTS 3,406,071 10/1968 Sus et al. ................ 544/159

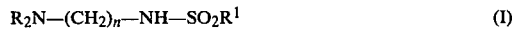

Primary Examiner—Richard A. Schwartz
Attorney, Agent, or Firm—Jacobs & Jacobs

[57] ABSTRACT

Compounds of the formula (I):

$$R_2N-(CH_2)_n-NH-SO_2R^1 \qquad (I)$$

and salts thereof wherein $NR_2$ represents a piperidyl, pyrrolidyl, or N-methylpiperazyl group any of which may be substituted by one or two methyl groups; $R^1$ is a 1-naphthyl group substituted by one or two moieties selected from fluorine, chlorine, bromine, methoxyl, ethoxyl, hydroxyl, acetoxyl, nitro, cyano, amino optionally substituted by one or two $C_{1-6}$ aklkyl groups, methyl, ethyl, carboxyl, methoxycarbonyl, ethoxycarbonyl, acetamido or carboxamido; and n is 2 or 3, pharmaceutical compositions containing them and a process for their preparation.

3 Claims, No Drawings

ANTI-ARRYTHMIC SULPHONAMIDE COMPOSITIONS

CROSS REFERENCE

This is a division of Ser. No. 148,139, filed May 9, 1980, now abandoned.

Various sulphonamides are known as chemical curiosities, see for example Braun et al, Annalen, 445, 253 (1925) or Curwain et al, J. Med. Chem., 14, 737 (1971), or as pharmaceutically active agents, see for example West German patent application No. 2623447, which relates to local anaesthetics, West German Patent Application No. 2710047 which relates to anti-anginal compounds, and West German patent application No. 2545496 which relates to platelet aggregation inhibitors.

However, none of these known sulphonamides has been reported as an anti-arrhythmic agent. It is desirable to provide anti-arrhythmic agents possessing low acute toxicity. A group of such compounds has now been found.

The present invention provides the compounds of the formula (I):

$$R_2N-(CH_2)_n-NH-SO_2R^1 \qquad (I)$$

and salts thereof wherein $NR_2$ represents a piperidyl, pyrrolidyl, or N-methylpiperazyl group any of which may be substituted by one or two methyl groups; $R^1$ is a 1-naphthyl group optionally substituted by one or two moieties selected from fluorine, chlorine, bromine, methoxyl, ethoxyl, hydroxyl, acetoxyl, nitro, cyano, amino optionally substituted by one or two $C_{1-6}$ alkyl groups, methyl, ethyl, carboxyl, methoxycarbonyl, ethoxycarbonyl, acetamido or carboxamido; and n is 2 or 3.

A group of compounds within those of the formula (I) consists of those wherein $R^1$ is a 1-naphthyl group optionally substituted by one or two moieties selected from fluorine, chlorine, bromine, methoxyl, ethoxyl, hydroxyl, acetoxyl, nitro, cyano, amino, methyl, ethyl, methoxycarbonyl, ethoxycarbonyl, acetamido or carboxamido.

Apt values for $NR_2$ include piperidyl, pyrrolidyl, 2-methylpyrrolidyl, 3-methylpyrrolidyl, 2,3-dimethylpyrrolidyl, 2,4-dimethylpyrrolidyl, 2,5-dimethylpyrrolidyl, and N-methylpiperazyl. More suitably the dimethylpyrrolidyl groups are in the form of their cis isomers.

Favoured values for $NR_2$ include the 2,6 and 3,5-dimethylpiperidyl, pyrrolidyl, 2,4- and cis-2,5-dimethylpyrrolidyl and N-methylpiperazyl groups, more favourably the cis-2,4- and cis-2,5-dimethylpyrrolidyl and N-methylpiperazyl groups. A highly favoured value for $NR_2$ is the cis-2,4-dimethylpyrrolidyl group as is 2-methylpiperidyl.

n is 2 or 3.

Particularly apt groups $R^1$ in respect of formula (I) include 1-naphthyl and 1-naphthyl monosubstituted by one of the previously named suitable substituents.

Certain favoured groups $R^1$ in respect of formula (I) include 1-naphthyl and 1-naphthyl substituted by a moiety selected from methyl, methoxyl, methoxycarbonyl or ethoxycarbonyl and amino optionally substituted by one or two $C_{1-6}$ alkyl groups. Preferred substituents include methoxyl and amino optionally substituted by one or two methyl groups. Suitable 1-naphthyl substitution positions include the 4- and 5-positions.

A preferred value for $R^1$ in respect to formula (I) is the 1-naphthyl group.

From the foregoing it will be realised that certain favoured compounds of this invention include those of the formula (II):

$$R^1{}_2N-(CH_2)_n-NH-SO_2-R^1 \qquad (II)$$

and salts thereof, wherein n and $R^1$ are as defined in relation to formula (I) and $R^1{}_2N$ is cis-2,4-dimethylpyrrolidyl, cis-2,5-dimethylpyrrolidyl or 4-methyl-piperazyl.

n is preferably 2 when $R^1{}_2N$ is cis-2,4- or cis-2,5-dimethylpyrrolidyl. n is preferably 3 when $R^1{}_2N$ is N-methyl-piperazyl.

Particularly apt, favoured and preferred $R^1$ are also so described under formula (I).

Cis-2,4-dimethylpyrrolidyl is a highly favoured value for $R^1{}_2N$ as is 2-methylpiperidyl.

Certain especially suitable compounds of this invention include those of the formula (III):

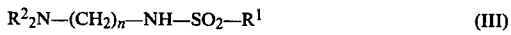
$$R^2{}_2N-(CH_2)_n-NH-SO_2-R^1 \qquad (III)$$

and salts thereof, wherein n and $R^1$ are as defined in relation to formula (I) and $R^2{}_2N$ is cis-2,4-dimethylpyrrolidyl or 2-methylpiperidyl.

n is preferably 2.

Particularly apt, favoured and preferred $R^1$ are as so described under formula (I).

From the foregoing it will be realised that certain favoured compounds of the invention are those of the formula (IV):

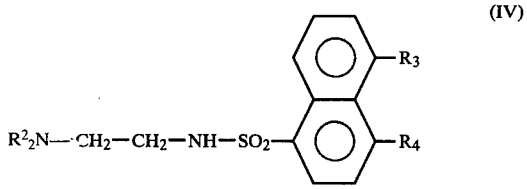

and salts thereof, wherein $R^2{}_2N$ is cis-2,4-dimethylpyrrolidyl and one of $R_3$ and $R_4$ is hydrogen and the other is hydrogen methoxyl or amino optionally substituted by one or two methyl groups.

Preferred compounds of this invention include: cis-2,4-dimethyl-1-[2-(1'-naphthalenesulphonamido)ethyl]-pyrrolidine;
cis-2,4-dimethyl-1-[2-(4'-methoxy-1'-naphthalenesulphonamido)ethyl]pyrrolidine;
cis-2,5-dimethyl-1-[2-(1'-naphthalenesulphonamido)ethyl]pyrrolidine; and
4-methyl-1-[3-(1'-naphthalenesulphonamido)propyl]-1,4-piperazine;
and salts thereof.

Particularly preferred compounds of this invention are cis-2,4-dimethyl-1-[2-(1'-naphthalenesulphonamido)-ethyl]pyrrolidine and 2-methyl-1-[3-(5'-dimethylamino-1'-naphthalenesulphonamido)propyl]-piperidine and salts thereof.

It will of course be realised that when $NR_2$ in the compounds of the formula (I) is asymmetrically substituted by one methyl group, the $NR_2$ group has a chiral centre. Compounds of the formula (I) containing such $NR_2$ groups are thus capable of existing in enantiomeric forms.

When $NR_2$ in the compounds of the formula (I) is substituted by two methyl groups, the $NR_2$ group has chiral centres. Compounds of the formula (I) containing such $NR_2$ groups are thus capable of existing in a number of stereoisomeric forms.

The invention extends to each of the steroisomeric forms, including enantiomers, of the compounds of the formula (I) and to mixtures therof, including racemates. The different stereoisomeric forms may be separated one from the other by the usual methods, or any given isomer may be obtained by stereospecific or asymmetric synthesis.

The salts of the compounds of the formulae (I), (II), (III) and (IV) include acid addition salts and these are preferably acid addition salts with pharmaceutically acceptable acids. Such acids may be inorganic or organic acids such as hydrochloric, hydrobromic, sulphuric, methanesulphonic, acetic, citric, lactic, tartaric, propionic, benzoic, fumaric and the like.

The salts of the compounds of the formulae (I), (II), (III) and (IV) also include pharmaceutically acceptable quaternary ammonium salts. Examples of such salts include such compounds quaternised by compounds such as $R_5$—Y wherein $R_5$ is $C_{1-6}$ alkyl, phenyl—$C_{1-6}$ alkyl or $C_{5-7}$ cycloalkyl, and Y is an anion of an acid. Suitable examples of $R_5$ include methyl, ethyl and n- and iso-propyl; and benzyl and phenylethyl. Suitable examples of Y include the halides such as chloride, bromide and iodide.

Examples of salts also include pharmaceutically acceptable internal salts such as N-oxides.

Compounds of the formula (I) which contain an $R^1$ carboxyl substituent may form salts at the carboxyl group. These are preferably salts with pharmaceutically acceptable metals or optionally substituted ammonium. Suitable metals include alkali metals and alkaline earth metals preferably sodium or potassium. Suitable optionally substituted ammonium ions include ammonium and pharmaceutically acceptable amine salts.

The present invention also provides a pharmaceutical composition which comprises a compound of the formula (I) or a salt thereof as hereinbefore defined and a pharmaceutically acceptable carrier.

The composition of this invention may be adapted for administration by mouth or by injection. Most suitably the composition will be in unit-dose form and such unit-doses will normally contain from 1 mg to 100 mg and more usually from 2 mg to 50 mg of the active agent.

These compositions may be administered 1 to 6 times daily or more usually 2 to 4 times daily in such manner that the daily dose for a 70 kg adult is about 1 mg to 250 mgs and more usually 5 mg to 200 mg, for example 10 mgs to 75 mgs. The compositions of this invention may be fabricated in conventional manner, for example they may be presented as tablets or capsules for oral administration or as dry powders sealed into ampoules for reconstitution with water or saline for injection. Tablets and capsules may contain carriers such as disintegrants, binders, lubricants, colourants and the like in conventional manner. They may therefore contain such agents as microcrystalline cellulose, lactose, starch, polyvinylpolypyrrolidone, sodium starch glycollate, magnesium stearate and the like. Tablets may be prepared by conventional mixing and compressing operations and capsules may be prepared by conventional mixing and filling operations.

The invention also provides a method of treatment or prophylaxis of cardiac arrhythmia in humans, comprising the administration to a sufferer of a therapeutically effective amount of a compound of the formula (I):

$$R_2N\text{—}(CH_2)_n\text{—}NH_2 \qquad (V)$$

wherein $R_2$ and n are as defined in relation to formula (I) and a compound of the formula (VI):

$$Cl\text{—}SO_2\text{—}R^1 \qquad (VI)$$

or a chemical equivalent thereof, wherein $R^1$ is as defined in relation to formula (I); and optionally forming a salt of the resultant compound of the formula (I).

Chemical equivalents of the compounds of formula (VI) include the corresponding bromide and iodide.

The preceding condensation reaction is generally effected at ambient temperature and normal pressure in a convenient solvent such as benzene or toluene. Removal of the solvent, for example by evaporation, yields the initial crude product which may then be purified by crystallisation, chromatography or the like to yield the salt in pure form. If desired this salt may then be converted into the free base by neutralisation and if desired the free base may be salified in conventional manner. The reaction may be carried out in the presence of a base to yield the desired compound as a free base.

It will be realised that, when $R^1$ is a substituted 1-naphthyl group in a compound of the formula (I), interconversion of suitable substituents may be carried out by conventional methods after formation of a compound of the formula (I). By way of example an acetamido group may be converted to an amino group, an alkoxyl or acetoxyl group may be converted to a hydroxyl group, a nitro group may be reduced to an amino group, or an alkoxycarbonyl group may be hydrolysed to a carboxyl group, all by conventional methods. Accordingly it will be realised that compounds of the formula (I) containg a substituent on the 1-naphthyl group which is convertible to another $R_2$ or $R_3$ group are useful intermediates and as such form an important aspect of the invention.

It will also be realised that salts of the compounds of the formula (I) which are not pharmaceutically acceptable may be useful as intermediates in the preparation of pharmaceutically acceptable salts of compounds of the formula (I) or the compounds of the formula (I) themselves, and as such form an aspect of the present invention.

When $NR_2$ in the compounds of the formula (I) is substituted by two methyl groups, these may be mutually cis or trans about the $NR_2$ ring. A mixture of cis and trans isomers of the compound of the formula (I) may be synthesised non-stereospecifically and the desired isomer separated conventionally therefrom, e.g. by chromatography; or alternatively the cis or trans isomer may if desired be synthesised from the corresponding cis or trans form of the compound of the formula (VI).

Cis- and trans-forms of the compound of the formula (VI) are either known as separate forms or may be separated conventionally e.g. by chromatography.

Racemates of compounds of the formula (I) wherein $NR_2$ is substituted by one or two methyl groups may be resolved conventionally, e.g. by salification with a chiral acid and separation of the resultant salts.

The following Examples illustrate the invention.

EXAMPLE I

2,4-Dimethyl-1-[2-(1'-naphthalenesulphonamido)ethyl]-pyrrolidine (1)

A solution of 2,4-dimethyl-1-(2-aminoethyl)pyrrolidine (7.2 g) in benzene (20 ml) was added dropwise while stirring to a solution of 1-naphthalenesulphonyl chloride (11.3 g, 0.05 mol) in benzene (60 ml). The mixture was stirred for a further 48 hours at room temperature whereby the reaction product separated as a brown, viscous oil which set and hardened to an amorphous mass. The benzene mother liquor was decanted, and the residue was dissolved in boiling isopropanol (500 ml) and treated with activated charcoal. After cooling the reaction product once again separated as a viscous oil. The isopropanolic solution was evaporated, and the residue was dissolved in water. The solution was adjusted to pH 9–10 with caustic soda solution and extracted with diethylether (3×100 ml). The extracts were combined, dried over $Na_2SO_4$ and evaporated to dryness. The residue was extracted with petroleum ether (700 ml) (40°–60° C.) After evaporating a solvent, the reaction product (10 g) was left as a free base. (Yield=60% of theoretical).

Bis{2,4-dimethyl-1-[2-(1'-naphthalenesulphonamido)ethyl]pyrrolidinium}fumarate cis isomer (2)

Fumaric acid (0.88 g) was added to a boiling solution of 2,4-dimethyl-1-(2-[1'-naphthalenesulphonamidoethyl)pyrrolidine] (5 g, 0.015 mol) in absolute ethanol (150 ml). After cooling, the reaction product separated as crystals. Finally, the salt was recrystallized from absolute ethanol (200 ml).

M.p. 160°–161° C., Mol. Wt 780,98; $C_{36}H_{48}N_4O_4S_2.C_4H_4O_4$. Yield=41% of theoretical. Satisfactory analytical data were obtained.

The trans isomer (3) was similarly prepared from the corresponding 2-aminoethylpyrrolidine derivative trans isomer.

EXAMPLE II

1-[3-(1'-Naphthalenesulphonamido)propyl]-pyrrolidine (5)

At room temperature, a solution of 1-(3-aminopropyl)pyrrolidine (6.4 g) in benzene (20 ml) added dropwise to a solution of 1'-naphthalenesulphonylchloride (11.3 g, 0.05 mol) in benzene (60 ml). The reaction mixture was stirred for a further three hours at room temperature and thereafter heated under reflux for half an hour. The oily separated reaction product did not crystallize on cooling. The benzene solution was decanted, and the remaining oil was dissolved in water. The solution was adjusted to pH 9,5 with caustic soda solution, extracted with diethyl ether (5×100 ml) and finally with chloroform (2×100 ml). The organic extracts were combined and dried over $Na_2SO_4$. After the solvent had been removed, the reaction product was left as a free base and was recrystallized from absolute ethanol (100 ml) to afford the crystalline product (7.2 g).

M.p. 122°–124° C., Mol. Wt. 318.4; $C_{17}H_{22}N_2O_2S$. Yield=45% of theoretical. Satisfactory analytical data were obtained.

2-Methyl-1-[3-(1'-naphthalenesulphonamido)propyl]-piperidine (7) was prepared analogously.

EXAMPLE III

1-[2-(1'-Naphthalenesulphonamido)ethyl]-pyrrolidinium chloride (6)

Whilst stirring, a solution of 1-(2-aminopropyl)pyrrolidine (5,7 g) in benzene (20 ml) was added dropwise to a solution of 1-naphthalenesulphonylchloride (11,3 g) in benzene (80 ml). The reaction mixture was stirred for a further eight hours at room temperature, whereby the reaction product crystallized from the mixture as the chloride. The precipitate was removed by suction and washed with benzene on the filter. Crude chloride was recrystallized from isopropanol (100 ml) to obtain the product (8.7 g).

M.p. 187°–188° C. Yield=67.5% of theoretical. Satisfactory analytical data were obtained.

The following compounds were prepared analogously:

2,6-dimethyl-1-[2-(1'-naphthalenesulphonamido)ethyl]-piperidinium chloride (8).

M.p. 194° C.; Yield=74% of theoretical.

4-methyl-1-[3-(1'-naphthalenesulphonamido)propyl]-1,4-piperazinium chloride (9).

M.P. 195° C.; Yield=78% of theoretical.

1-[2-(1'-naphthalenesulphonamido)ethyl]piperidinium chloride (12).

M.p. 192°–194° C.; Yield=62% of theoretical.

2,4-dimethyl-1-[2-(4'-methoxynaphthelene-1'-sulphonamido)ethyl]pyrrolidinium chloride (19).

M.P. 181°–183° C.; Yield=63% of theoretical. Satisfactory analytical data were obtained in all cases.

EXAMPLE IV

2,4-Dimethyl-1-[3-(1'-Naphthalenesulphonamido)-propyl]pyrrolidine (4)

At room temperature, a solution of 1-(3-aminopropyl)2,4-dimethylpyrrolidine (7,8 g) in benzene (20 ml) was added dropwise to a solution of 1-naphthalenesulphonylchloride (11.3 g, 0.05 mol) in benzene (60 ml). The reaction mixture was stirred for a further three hours at room temperature and thereafter warmed under reflux for half an hour. The oily separated reaction product did not crystallize on cooling. The benzene solution was decanted, and the remaining oil was dissolved in water. The solution was adjusted to pH 9,5 with caustic soda solution, extracted with diethyl ether (5×100 ml) and finally with chloroform (2×100 ml). The organic extracts were combined and dried over $Na_2SO_4$. After the solvent had been removed, the reaction product was left as a free base and was recrystallized from ethanol/water (25 ml ethanol; water dropwise till the first precipitate was observed) to afford the crystalline product (8,6 g).

M.p. 82°–83° C., mol. Wt. 346,5 $C_{19}H_{26}N_2O_2S$. Yield=49,7% of theoretical. Satisfactory analytical data were obtained.

[3-(8'-chloro-1'-Naphthalenesulphonamido)propyl]-pyrrolidine (18) was prepared analogously.

M.p. 143°–145° C.; Yield=37% of theoretical.

EXAMPLE V

Cis- (10) and trans- (11) 2,5-dimethyl-1-[2-(1'-naphthalenesulphonamidoethyl]-pyrrolidinium chloride 2,5-dimethyl-1-(2-aminoethyl)pyrrolidine (5 g 0,035 mol) in toluene (20 ml) was added dropwise at room temperature to a solution of 1-naphthalenesulphonylchloride (8,2 g 0,035 mol) in toluene (180 ml). The mixture was stirred 24 hours at room temperature. Thereafter, the mixture was neutralized with Na₂CO₃ solution (3.73 g in 100 ml). The organic layer was separated off, dried over Na₂SO₄, and the solvent was removed by distillation. The residue (12 g cis-trans product isomer mixture) was purified and separated over silica gel (14 g) by elution with chloroform: methanol: conc.ammonia solution 190:9:1.

Fraction I: 4500 ml—1-naphthalenesulphonylchloride;

Fraction II: 140 ml—product A;

Fraction III: 120 ml—mixture of product A and product B;

Fraction IV: 1500 ml—product B.

After the solvent was removed, the residue of Fraction II (6 g) was dissolved in ethyl acetate and hydrogen chloride gas was passed through this solution. The resulting brownish precipitate was dissolved in boiling isopropanol and the solution was decolorized with charcoal. After filtration and cooling the filtrate, (10) crystallized out and was filtered off (3.7 g Mp 193° C.). Fraction IV was treated in the same way, to yield (11) (1.8 g. Mp 216° C.).

(10): NMR: 1,34 ppm (6 H,d: J 6,5 Hz 2 CH₃) cis-isomer.

(11): NMR 1,03 ppm (3 H,d: J 7 Hz, CH₃) 1,24 ppm (3 H,d: J 6,5 Hz, CH₃) trans isomer.

The following were prepared and separated analogously. Cis- (14) and trans- (13) 3,5-dimethyl-1-[2-(1'-naphthalenesulphonamido)ethyl]piperidinium chloride.

(14): M.p. 254° C.

(13): M.p. 191° C. Satisfactory analytical data were obtained in all cases.

EXAMPLE VI

1-[2-(5-dimethylamino-1-naphthalenesulphonamido)ethyl]-2,4-dimethylpyrrolidinium chloride (15)

A solution of 1-(2-aminoethyl)-2,4-dimethyl (7.2 g, 0.05 mole) in toluene was added with stirring to a solution of 5-dimethylamino-1-naphthalenesulphonylchloride (13.5 g, 0.05 mole) in toluene (200 ml). The reaction mixture was stirred for 24 hr at room temperature thereafter, water (200 ml) was added, and the pH was adjusted to 10. The organic layer was separated off and dried over sodium sulphate. Hydrogen chloride gas was passed through this solution. The resulting precipitate (17 g) was recrystallised twice from isopropanol to obtain the product (6.8 g). M.p. 175°–177° C.

Yield = 33% of theoretical.

The following were prepared analogously:
1-[3-(5-dimethylamino-1-naphthalenesulphonamido)-propyl]-2-methylpiperidinium fumarate (16),
bis{1-[2-(8-chloro-1-naphthalenesulphonamido)ethyl]-2,4-dimethylpyrrolidinium}fumarate (17),
1-[2-(7-methyl-1-naphthalenesulphonamido)ethyl]-2,4-dimethylpyrrolidinium chloride (19)
1-[2-(7-methyl-1-naphthalenesulphonamido)ethyl]-2,4-dimethylpyrrolidinium chloride (20)
using fumaric acid in place of hydrogen chloride as appropriate.

Satisfactory analytical data were obtained in all cases.

DESCRIPTION 1

Pharmacology of Compounds

Test Procedure to Demonstrate Antiarrythmic Effects

Electrostimulation Test

According to the method described by Szekeres, L. and Papp, G. J., (Naunyn-Schmiedebergs Arch. exp. Path. Pharmak. 245, 70 (1963), arrhythmias are induced in Guinea pigs by electrostimulation of the right ventricle of the heart. The animals are anesthetized with Urethane (1.2 g/kg i.p.) and artificially respired before a needle electrode is inserted in the right ventricle of the heart. Substances are given intraduodenally 30 min before the stimulation. The voltage needed for induction of extrasystoles in control animals (n=6) is compared with that required for induction of arrhythmias in treated animals (n=6). The difference is statistically evaluated by the unpaired t-test (Student).

This method was used to evaluate the compounds of the present invention. The results are shown in following Tables 1 to 3.

A blank in the last column indicates data not available. * means statistically significant p <0.05.

TABLE 1

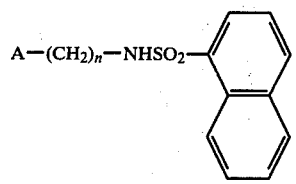

| COMPOUND NO. | A | n | Salt | Mp °C. | Yield % | % Increase of Voltage/ Electrostimulation Test Dose mg/kg i.d. (GP; n = 6) |
|---|---|---|---|---|---|---|
| 2 | cis 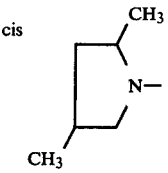 | 2 | ½ C₄H₄O₄ EtOH | 161 | 57,4 | 55.4* |

TABLE 1-continued

A—(CH₂)ₙ—NHSO₂—[naphthyl]

| COMPOUND NO. | A | n | Salt | Mp °C. | Yield % | % Increase of Voltage/ Electrostimulation Test Dose mg/kg i.d. (GP; n = 6) |
|---|---|---|---|---|---|---|
| 4 | 2,4-dimethylpiperidin-1-yl (CH₃ at 2 and 4) | 3 | — | 82–83 EtOH | 49,7 | 2,4 |
| 5 | pyrrolidin-1-yl | 3 | — | 122–124 EtOH | 45,3 | 23,4* |
| 6 | pyrrolidin-1-yl | 2 | HCl | 187–188 IPA | 67,5 | 4,48 |
| 8 | 2,6-dimethylpiperidin-1-yl | 2 | HCl | 194 EtOH | 74 | 16,4* |
| 9 | 4-methylpiperazin-1-yl | 3 | HCl | 195 EtOH | 78 | 31,8* |
| 10 | cis-2,5-dimethylpyrrolidin-1-yl | 2 | HCl | 193 IPA | 31 | 30* |
| 12 | piperidin-1-yl | 2 | HCl | 192–194 H₂O | 61,6 | |
| 13 | trans-3,5-dimethylpiperidin-1-yl | 2 | HCl | 191 IPA | 14 | |

TABLE 1-continued
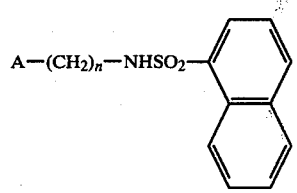
| COMPOUND NO. | A | n | Salt | Mp °C. | Yield % | % Increase of Voltage/ Electrostimulation Test Dose mg/kg i.d. (GP; n = 6) |
|---|---|---|---|---|---|---|
| 14 | CH₃ ... cis ... N— ... H₃C | 2 | HCl | 254 EtOH | 41 | |
TABLE 2
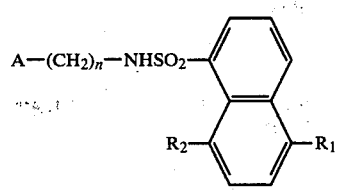
| COMPOUND No. | A | n | R₁ | R₂ | Salt | MP °C. | Yield | % Increase of Voltage/ Electrostimulation Test Dose mg/kg i.d. (GP; m = 6) |
|---|---|---|---|---|---|---|---|---|
| 15 | CH₃ / N / CH₃ | 2 | —N(CH₃)₂ | H | HCl | 175–177 IPA | 33 | 20.0* |
| 16 | CH₃ / N | 3 | —N(CH₃)₂ | H | C₄H₄O₄ | 117 IPA | 40 | 51.5* |
| 18 | N | 3 | H | Cl | — | 143–145 | 20 | |

TABLE 3

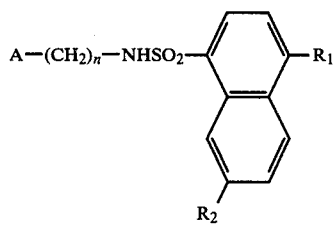

| COMPOUND No. | A | n | $R_1$ | $R_2$ | Salt | Mp °C. | Yield % | % Increase of Voltage/Electrostimulation Test Dose mg/kg i.d. (GP; n = 6) |
|---|---|---|---|---|---|---|---|---|
| 19 |  | 2 | $OCH_3$ | H | HCl | 181–183 | 63 | 30,3* |
| 20 |  | 2 | H | $CH_3$ | HCl | 184 | 70 |  |

Toxicity

No toxic effects were observed at the test dosages.

I claim:

1. An anti-arrythmic composition comprising a carrier and an anti-arrythmic amount of a compound of the formula (I):

$$R_2N\text{---}(CH_2)_n\text{---}NH\text{---}SO_2R^1 \qquad (I)$$

or a pharmaceutically acceptable salt or acid addition salt with a pharmaceutically acceptable acid, wherein $NR_2$ is 2,6- or 3,5-dimethylpiperidyl, pyrrolidyl, cis-2,4- or cis-2,5-dimethylpyrrolidyl, N-methylpiperazyl or 2-methylpiperidyl; n is 2 or 3; and $R^1$ is 1-naphthyl unsubstituted or substituted by methyl, methoxyl, methoxycarbonyl or ethoxycarbonyl or amino optionally substituted by one or two $C_{1-6}$ alkyl groups.

2. An anti-arrythmic composition comprising a carrier and an anti-arrythmic amount of a compound of the formula (I):

$$R_2N\text{---}(CH_2)_n\text{---}NH\text{---}SO_2R^1 \qquad (I)$$

or a pharmaceutically acceptable salt or acid addition salt with a pharmaceutically acceptable acid, wherein $NR_2$ is 2,6- or 3,5-dimethylpiperidyl, pyrrolidyl, cis-2,4- or cis-2,5-dimethylpyrrolidyl, N-methylpiperazyl or 2-methylpiperidyl; n is 2 or 3; and $R^1$ is 1-naphthyl substituted by methoxyl or amino optionally substituted by one or two methyl groups.

3. An anti-arrythmic composition comprising a carrier and an anti-arrythmic amount of a compound of the formula (I):

$$R_2N\text{---}(CH_2)_n\text{---}NH\text{---}SO_2R^1 \qquad (I)$$

or a pharmaceutically acceptable salt or acid addition salt with a pharmaceutically acceptable acid, wherein $NR_2$ is 2,6- or 3,5-dimethylpiperidyl, pyrrolidyl, cis-2,4- or cis-2,5-dimethylpyrrolidyl, N-methylpiperazyl or 2-methylpiperidyl; n is 2 or 3; and $R^1$ is 1-naphthyl substituted by methoxyl or amino optionally substituted by one or two methyl groups, the 1-naphthyl being in the 4- or 5-position.

* * * * *